US00PP37064P2

(12) United States Plant Patent
Gardner et al.

(10) Patent No.: US PP37,064 P2
(45) Date of Patent: Oct. 28, 2025

(54) NECTARINE TREE NAMED 'Mike's Fire'

(50) Latin Name: ***Prunus persica* var. *nucipersica***
Varietal Denomination: Mike's Fire

(71) Applicants: Lacey Marie Gardner, Modesto, CA (US); Tracee Louise Bettencourt, Modesto, CA (US)

(72) Inventors: Lacey Marie Gardner, Modesto, CA (US); Tracee Louise Bettencourt, Modesto, CA (US)

( * ) Notice: Subject to any disclaimer, the term of this patent is extended or adjusted under 35 U.S.C. 154(b) by 0 days.

(21) Appl. No.: 18/831,590

(22) Filed: May 22, 2025

(51) Int. Cl.
*A01H 5/08* (2018.01)
*A01H 6/74* (2018.01)

(52) U.S. Cl.
USPC ..... Plt./190

(58) Field of Classification Search
USPC ..... Plt./187, 190, 192
See application file for complete search history.

*Primary Examiner* — Susan Mccormick Ewoldt

(57) ABSTRACT

A new and distinct variety of nectarine tree (*Prunus persica* var. *nucipersica*). The following features of the tree and its fruit are characterized with the tree budded on Nemaguard' Rootstock (non-patented), grown on Handford sandy loam soil with Storie Index rating 95, in USDA Hardiness Zone 9, near Modesto, California, with standard commercial fruit growing practices, such as pruning, thinning, spraying, irrigation and fertilization. Its novelty consist of the following combination of desirable features:

1. Tree being a regular and productive bearer of medium to large size fruit.
2. Tree having a vigorous, upright growth habit.
3. Clingstone fruit with firm, yellow flesh.
4. Fruit with very good flavor and eating quality.
5. Fruit with a high degree of attractive red skin color.

1 Drawing Sheet

Botanical designation: *Prunus persica* var. *nucipersica*.
Variety denomination: 'Mike's Fire'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, California.

Prior Varieties

Among the existing varieties of nectarine trees, which are known to us, and mentioned herein, 'Honey Diva' Nectarine (U.S. Plant Pat. No. 15, 291), 'Magic Fire' Nectarine (U.S. Plant Pat. No. 32,016) and the proprietary non-patented nectarine seedling selections '184BA574' and '359LY18'.

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was developed by us in our experimental orchard located near Modesto, California from a first generation cross between the proprietary non-patented nectarine seedling selection (184BA574) and 'Magic Fire' Nectarine (U.S. Plant Pat. No. 32,016). The proprietary non-patented nectarine seed parent '184BA574' originated as an open pollinated nectarine seedling from the proprietary non-patented nectarine seedling '359LY18'. A large number of these first generation crosses were planted and grown on their own root system. Under close and careful observation, we recognized the desirable tree and fruit characteristics of the present seedling and selected it in 2018 for additional asexual propagation and commercialization.

ASEXUAL REPRODUCTION OF THE VARIETY

In 2018 asexual reproduction of the new and distinct variety of nectarine tree was by budding to 'Nemaguard' Rootstock (non-patented), as performed by us in our experimental orchard located near Modesto, California, and shows that reproductions run true to the original tree and all characteristics of the tree and its fruit are established and transmitted through succeeding asexual propagations.

SUMMARY OF THE NEW VARIETY

The present new and distinct variety of nectarine tree (*Prunus persica* var. *nucipersica*) is of large size, vigorous, upright growth and a regular and productive bearer of medium to large size, yellow flesh, clingstone fruit. The fruit is further characterized by its very good flavor and eating quality and having good storage and shipping ability. In comparison to its proprietary non-patented nectarine seed parent (184BA574) the fruit of the new variety is approximately 11 days later in maturity. In comparison to its pollen parent 'Magic Fire' (U.S. Plant Pat. No. 32,016) the fruit of the new variety is approximately 9 days later in maturity. In comparison to the commercial variety 'Honey Diva' Nectarine (U.S. Plant Pat. No. 15,291) the fruit of the new variety is approximately 11 days earlier in maturity.

DESCRIPTION OF THE PHOTOGRAPH

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 6 year old specimens grown near Modesto, California, with color in accordance with Munsell Book of Color published in 1958.

Tree:

*Size*.—Medium, usually pruned to 3 to 3.5 meters in height and width for economical harvesting of fruit. Size varies with different cultural practices.

*Vigor*.—Vigorous, growth of 1.5 to 2 meters in height the first growing season. Varies slightly with type and fertility of soil, climatic conditions and cultural practices.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 4 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 600 hours at or below 45° F.

Trunk:

*Size*.—Medium, average circumference 25.4 cm at 22.9 cm above ground on a 6 year old tree.

*Stocky*.—Medium stocky.

*Texture*.—Medium shaggy, roughness increases with age.

*Color*.—Varies from 2.5Y 5/2 to 2.5Y 3/2.

Branches

*Size*.—Medium. Average circumference 8.9 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 32 in a 25.8 square cm area. Average length 3.8 mm. Average width 1.7 mm. Color varies from 10YR 5/6 to 10YR 4/6.

*Color*.—New growth varies from 5GY 6/4 to 5GY 5/4. Mature growth varies from 10YR 4/4 to 10YR 2/2, varies with age of growth.

Leaves:

*Size*.—Large. Average length 124.2 mm. Average width 36.0 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 14.3 mm. Average width 1.5 mm. Longitudinally grooved. Surface — glabrous. Color varies from 10Y 7/6 to 10Y 6/6.

*Glands*.—Type — reniform. Size — small. Average length 1.0 mm. Average diameter 0.5 mm. Number varies from 1 to 4, average number 2. Located primarily on base of leaf blade and upper portion of the petiole. Color varies from 10Y 7/6 to 10Y 7/4.

*Stipules*.—None present at time of measurement.

*Color*.—Upper surface varies from 2.5GY 5/4 to 2.5GY 3/4. Lower surface varies from 2.5GY 6/4 to 2.5GY 5/4.Midvein color varies from 10Y 7/6 to 10Y 7/8.

Flower buds:

*Size*.—Large. Average length 19.7 mm. Average diameter 10.9 mm.

*Hardiness*.—Hardy with respect to California winters.

*Density*.—Medium dense.

*Form*.—Elongated.

*Pedicel*.—Average length 4.6 mm. Average width 1.6 mm. Surface — glabrous. Color varies from 5GY 6/8 to 5GY 5/6 with 5R 3/4.

*Color*.—Varies from 5RP 8/6 to 7.5RP 7/8.

Flowers:

*Blooming period*.—Date of First Bloom Feb. 23, 2024. Date of Petal Fall Mar. 5, 2024, varies slightly with climatic conditions.

*Size*.—Large. Average height 23.4 mm. Average diameter 56.0 mm.

*Petals*.—Normally 5, alternately arranged to sepals. Size — large. Average length 28.3 mm. Average width 19.6 mm. Petal apex — rounded. Petal base — truncate. Form — elliptical. Arrangement — slightly overlapping. Margin — sinuate. Both upper and lower surface glabrous. Color varies from 5RP 8/4 to 7.5RP 8/4, fades with age of flower.

*Sepals*.—Normally 5, alternately arranged to petals. Size — large. Average length 7.9 mm. Average width 6.1 mm. Sepal apex — ovate to triangular. Shape — ovate. Margin — entire. Surface — upper surface glabrous, lower surface pubescent. Color — upper surface varies from 5GY 5/6 to 5R 3/4. Lower surface varies from 2.5R 3/2 to 5R 2/4.

*Stamens*.—Average number per flower 43. Average filament length 18.2 mm. On average the stamens are above the height of the petals. Filament. color varies from N 9.5/(white) to 5RP 6/6. Anther color varies from 7.5R 3/12 to 5Y 8/10.

*Pollen*.—Self fertile. Color varies from 2.5Y 7/10 to 5Y 7/12.

*Pistil*.—Number — normally one. Average length 24.0 mm. Position of stigma even with anthers. Surface — glabrous. Color varies from 10Y 8/8to 2.5GY 8/6.

*Fragrance*.—Slight.

*Color*.—Varies from 5RP 8/4 to 7.5RP 8/4.

*Pedicel*.—Average length 6.1 mm. Average width 1.5 mm. Color varies form 2.5GY 5/8 to 5GY 5/8.

*Number flowers per flower bud*.—Normally one.

Fruit:

*Maturity when described*.—Firm ripe and ready for consumption.

*Date of first picking*.—Aug. 2, 2024.

*Date of last picking*.—Aug. 12, 2024, varies slightly with climatic conditions.

*Size*.—Medium to large. Average diameter axially 65.4 mm. Average transversely in suture plane 62.9 mm. Average weight 153.4 grams, varies slightly with fertility of the soil, amount of thinning and climatic conditions.

*Form*.—Globose to slightly elongated.

*Suture*.—Slightly lipped, extends from base to apex.

*Ventral surface*.—Slightly lipped.

*Apex*.—Slightly retuse.

*Base*.—Slightly retuse.

*Stem cavity*.—Rounded to slightly elongated in suture plane. Average depth 9.4 mm. Average diameter 10.0 mm.

Stem:

*Size*.—Small to medium. Average length 9.4 mm. Average diameter 2.8 mm.

*Color*.—Varies from 7.5Y 6/8 to 10Y 5/6.

Flesh:

*Ripens*.—Evenly to slightly early at apex.

*Texture*.—Firm, meaty, crisp.

*Fibers*.—Few, small, tender.

*Firmness*.—Very good, comparable to other commercial nectarine varieties.

*Aroma*.—Moderate.

*Amydgalin*.—Undetected. Amydgalin:

*Eating quality*.—Very good.

*Flavor*.—Very good, with a good balance between acid and sugar.

*Juice*.—Moderate amount, enhances flavor.

*Acidity*.—Not available.

*Brix*.—Average Brix 14.5°, varies slightly with amount of fruit per tree and climatic conditions.

*Color*.—Varies from 2.5Y 8/10 to 2.5Y 8/12.

*Pit cavity*.—Average length 41.1 mm. Average width 27.2 mm. Average depth 12.2 mm. Color varies from 7.5R 3/8 to 7.5R 2/8.

Skin:

*Thickness*.—Medium.

*Surface*.—Smooth.

*Bloom*.—Wanting.

*Tendency to crack*.—None.

*Color*.—Ground color varies from 2.5Y 7/10 to 7.5YR 6/12. Overspread with 5R 2/8 to 5R 3/10.

*Tenacity*.—Tenacious to the flesh.

*Astringency*.—Slight to none.

Stone:

*Type*.—Clingstone, strong adherence to flesh.

*Size*.—Large. Average length 38.3 mm. Average width 26.6 mm. Average thickness 18.1 mm.

*Form*.—Obovoid.

*Base*.—Flat.

*Apex*.—Pointed. Average length 1.9 mm.

*Surface*.—Pitted throughout, pits vary from round to elongated.

*Sides*.—Unequal, one side extending further outward from suture plane.

*Ridges*.—Relatively smooth, narrow ridges extending from base to apex.

*Tendency to split*.—None.

*Color*.—Varies from 5R 2/6 to 7.5R 3/8 when dry.

Kernel:

*Size*.—Large. Average length 19.9 mm. Average width 11.7 mm. Average depth 5.5 mm.

*Form*.—Ovate.

*Viability*.—Viable, complete embryo development.

*Skin color*.—Varies from 2.5Y 8/8 to 2.5Y 8/10.

Use: Dessert. Market—local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, California, no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, California.

The invention claimed is:

1. A new and distinct variety of nectarine tree named 'Mike's Fire' substantially as illustrated and described.

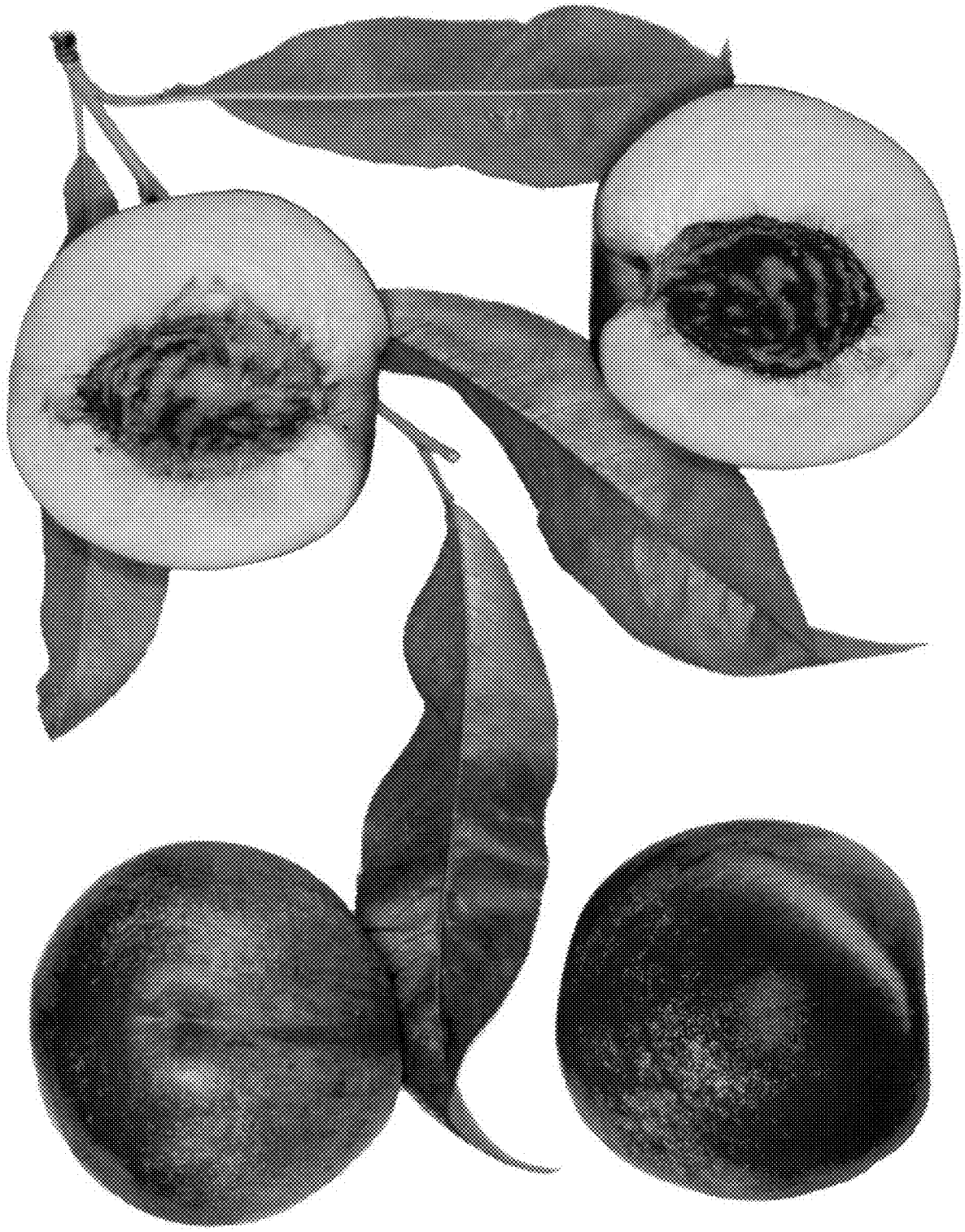

* * * * *